US011667855B2

(12) United States Patent
Hwang et al.

(10) Patent No.: US 11,667,855 B2
(45) Date of Patent: Jun. 6, 2023

(54) METHOD OF PRODUCING AROMATIC HYDROCARBONS

(71) Applicant: LG CHEM, LTD., Seoul (KR)

(72) Inventors: Sung June Hwang, Daejeon (KR); Tae Woo Kim, Daejeon (KR); Sung Kyu Lee, Daejeon (KR)

(73) Assignee: LG CHEM, LTD, Seoul (KR)

( * ) Notice: Subject to any disclaimer, the term of this patent is extended or adjusted under 35 U.S.C. 154(b) by 117 days.

(21) Appl. No.: 17/428,932

(22) PCT Filed: Nov. 9, 2020

(86) PCT No.: PCT/KR2020/015586
§ 371 (c)(1),
(2) Date: Aug. 5, 2021

(87) PCT Pub. No.: WO2021/256624
PCT Pub. Date: Dec. 23, 2021

(65) Prior Publication Data
US 2022/0306950 A1 Sep. 29, 2022

(30) Foreign Application Priority Data

Jun. 16, 2020 (KR) .................. 10-2020-0072866
Oct. 28, 2020 (KR) .................. 10-2020-0141047

(51) Int. Cl.
*C10G 67/02* (2006.01)
*B01D 3/40* (2006.01)
(Continued)

(52) U.S. Cl.
CPC .............. *C10G 67/02* (2013.01); *B01D 3/143* (2013.01); *B01D 3/40* (2013.01); *B01D 5/006* (2013.01);
(Continued)

(58) Field of Classification Search
None
See application file for complete search history.

(56) References Cited

U.S. PATENT DOCUMENTS 3,316,318 A * 4/1967 Voetter ............... C10G 67/0427
208/264
3,684,665 A * 8/1972 Hisao Abe et al. ..... C10G 7/08
203/64
(Continued)

FOREIGN PATENT DOCUMENTS

JP  2008-543893 A  12/2008
JP  2011-137032 A   7/2011
(Continued)

OTHER PUBLICATIONS

H. Kubo et al., "Make BTX From Cracker Gasoline", Hydrocarbon Processing, Gulf Publishing Co., Houston, US, vol. 49, No. 7, Jul. 1, 1970, pp. 111-113, XP001048454.
(Continued)

*Primary Examiner* — Tam M Nguyen
(74) *Attorney, Agent, or Firm* — Dentons US LLP (57) ABSTRACT

A method of producing aromatic hydrocarbons including: supplying a raw material stream to a C6 separation column, supplying an upper discharge stream from the C6 separation column to a first gasoline hydrogenation unit, and supplying a lower discharge stream from the C6 separation column to a C7 separation column; supplying an upper discharge stream from the C7 separation column to the first gasoline hydrogenation unit and supplying a lower discharge stream from the C7 separation column to a C8 separation column; separating benzene and toluene from a discharge stream from the first gasoline hydrogenation unit; removing a lower discharge stream from the C8 separation column and supplying an upper discharge stream from the C8 separation column to a second extractive distillation column; and separating styrene from a lower discharge stream from the second extractive distillation column and separating xylene from an upper discharge stream from the second extractive distillation column.

14 Claims, 4 Drawing Sheets

(51) Int. Cl.
*C07C 7/08* (2006.01)
*B01D 3/14* (2006.01)
*B01D 5/00* (2006.01)
*C07C 7/00* (2006.01)
*C07C 7/163* (2006.01)
*C10G 53/16* (2006.01)

(52) U.S. Cl.
CPC ............ *B01D 5/0075* (2013.01); *C07C 7/005* (2013.01); *C07C 7/08* (2013.01); *C07C 7/163* (2013.01); *C10G 53/16* (2013.01); C10G 2400/30 (2013.01)

(56) References Cited

U.S. PATENT DOCUMENTS

| | | | |
|---|---|---|---|
| 4,009,218 A * | 2/1977 | Uitti | C02F 1/26 |
| | | | 585/867 |
| 4,097,371 A | 6/1978 | Giroux | |
| 10,392,322 B2 * | 8/2019 | Bender | B01D 3/141 |
| 2008/0194900 A1 | 8/2008 | Bhirud | |
| 2011/0048922 A1 * | 3/2011 | Cretoiu | B01D 3/38 |
| | | | 202/160 |
| 2014/0364664 A1 * | 12/2014 | Chuang | C07C 7/14891 |
| | | | 585/254 |
| 2018/0170831 A1 | 6/2018 | Jan et al. | |
| 2022/0306951 A1 * | 9/2022 | Hwang | C07C 7/04 |

FOREIGN PATENT DOCUMENTS

| | | |
|---|---|---|
| JP | 2012-509976 A | 4/2012 |
| KR | 10-0843436 B1 | 7/2008 |
| KR | 10-2013-0034821 A | 4/2013 |
| KR | 10-2013-0059042 A | 6/2013 |
| KR | 10-2015-0066586 A | 6/2015 |
| KR | 10-2016-0124871 A | 10/2016 |
| KR | 10-2017-0018426 A | 2/2017 |
| WO | 2016011521 A1 | 1/2016 |
| WO | 2019-105767 A1 | 6/2019 |

OTHER PUBLICATIONS

"Typical specifications after first stage hydrogenation", Oil & Gas Journal, vol. 77, No. 13, Mar. 26, 1979, p. 85, XP001270502.

* cited by examiner

METHOD OF PRODUCING AROMATIC HYDROCARBONS

CROSS-REFERENCE TO RELATED APPLICATIONS

This application is a U.S. national phase of international application No. PCT/KR2020/015586, filed on Nov. 9, 2020, and claims the benefit of priority to Korean Patent Application No. 10-2020-0072866 filed on Jun. 16, 2020, and Korean Patent Application No. 10-2020-0141047 filed on Oct. 28, 2020, the entire contents of which are incorporated herein as part of the specification.

TECHNICAL FIELD

The present invention relates to a method of producing aromatic hydrocarbons, and more particularly, to a method of producing benzene, toluene, and xylene (BTX) and styrene in a single process simultaneously, while also reducing energy consumption.

BACKGROUND

A naphtha cracking center (hereinafter, referred to as "NCC") is a process of pyrolyzing naphtha which is a fraction of gasoline at a temperature of about 950° C. to 1,050° C. to produce ethylene, propylene, butylene, and benzene, toluene, and xylene (BTX), and the like which are basic raw materials of petrochemical products.

Conventionally, raw pyrolysis gasoline (RPG) which is a by-product of a process of producing ethylene and propylene using naphtha as a raw material was used to produce BTX and styrene by separate processes.

The BTX production process was performed by largely including a gasoline hydrogenation (GHT, hydrodesulfurization) process, a prefraction (PF) process, and an extractive distillation process (EDP). In this case, the total amount of the raw material stream is supplied to the gasoline hydrogenation (GHT) process, thereby increasing an amount of hydrogen used due to an increase in a flow rate supplied to the gasoline hydrogenation (GHT). In addition, because the prefraction (PF) process for separating benzene, toluene, and xylene is performed after the gasoline hydrogenation (GHT) process, the process is complicated, and in particular, in the case of xylene, since the route for producing xylene from C8+ hydrocarbons remaining after separating prefractionated C8+ hydrocarbons, benzene, and toluene is long, the process is more complicated.

In addition, the styrene extractive distillation process is a process of directly producing styrene from RPG through an extractive distillation process (EDP), and may be positioned in a front end of the BTX production process. Here, a prefraction (PF) process step of RPG to C7− hydrocarbons, a C8 hydrocarbon, and C9+ hydrocarbons is performed beforehand to separate a C8 hydrocarbon before supplying the RPG to the EDP. However, in this case, they are mixed again because the separated C7− hydrocarbons and C8 hydrocarbon are introduced into the BTX production process and subjected to a gasoline hydrogenation (GHT) process step. After performing the GHT step, the C7− hydrocarbons and the C8 hydrocarbon are separated again in the BTX production process, and as such, performing a step of separating C7− hydrocarbons and a C8 hydrocarbon twice leads to a waste of process costs and energy.

SUMMARY

To solve the problems described above, an objective of the present invention is to provide a method which produces BTX and styrene in one process at the same time, while simplifying the process and reducing energy.

In one inventive aspect, a method of producing aromatic hydrocarbons includes: a step of supplying a raw material stream to a C6 separation column, supplying an upper discharge stream from the C6 separation column to a first gasoline hydrogenation unit, and supplying a lower discharge stream from the C6 separation column to a C7 separation column; a step of supplying an upper discharge stream from the C7 separation column to the first gasoline hydrogenation unit and supplying a lower discharge stream from the C7 separation column to a C8 separation column; a step of separating benzene and toluene from a discharge stream from the first gasoline hydrogenation unit; a step of removing a lower discharge stream from the C8 separation column and supplying an upper discharge stream from the C8 separation column to a second extractive distillation column; and a step of separating styrene from a lower discharge stream from the second extractive distillation column and separating xylene from an upper discharge stream from the second extractive distillation column, wherein an overhead stream of the C8 separation column exchanges heat with one or more streams in the process in one or more heat exchangers.

According to an exemplary method of producing aromatic hydrocarbons of the present invention, BTX and styrene may be produced in one process at the same time, and in this process, a prefraction process step which was required for the production of BTX may be omitted to reduce energy due to a decrease of an amount of steam used.

In addition, a C8 separation column is operated at 100 mmHg to 350 mmHg, thereby minimizing a side reaction in the C8 separation column and allowing heat exchange of an overhead stream of the C8 separation column with a stream in the process. Thus, a condensation heat of the overhead stream of the C8 separation column is used as a heat source of the stream in the process, thereby reducing process energy.

In addition, only a C7− hydrocarbon stream excluding C8+ hydrocarbons in the raw material stream is supplied to a first gasoline hydrogenation unit, thereby decreasing a flow rate supplied to the first gasoline hydrogenation unit to decrease an amount of hydrogen used in the first gasoline hydrogenation unit and increasing a catalyst lifetime.

In addition, a prefraction column and a xylene separation column are removed from a conventional BTX production process to simplify the process, and a second gasoline hydrogenation unit is installed to allow xylene to be directly produced from an upper discharge stream from a second extractive distillation column, thereby solving the problem of a complicated and long conventional production path for producing xylene.

In addition, the second gasoline hydrogenation unit is installed, whereby an unnecessary process of mixing an upper discharge stream from a second extractive distillation column with an upper discharge stream from a C7 separation column again, performing a hydrodesulfurization reaction in the first gasoline hydrogenation unit, and performing separation again, is not required.

DETAILED DESCRIPTION

The terms and words used in the description and claims of the present invention are not to be construed limitedly as having general or dictionary meanings but are to be construed as having meanings and concepts meeting the technical ideas of the present invention, based on a principle that the inventors are able to appropriately define the concepts of terms in order to describe their own inventions in the best mode.

In the present invention, the term "stream" may refer to a fluid flow in a process, or may refer to a fluid itself flowing in a pipe. Specifically, the "stream" may refer to both a fluid itself flowing in a pipe connecting each apparatus and a fluid flow. In addition, the fluid may refer to a gas or a liquid.

In the present invention, the term "overhead stream" may refer to a stream discharged from an upper portion of a distillation column before condensed (cooled) using a condenser and a heat exchanger, and the term "upper discharge stream" may refer to a stream after being passed through the condenser, a heat exchanger, and the like to be condensed (cooled).

In the present invention, the term "bottom stream" may refer to a stream discharged from a lower portion of the distillation column before heated using a reboiler and a heat exchanger, and the term "lower discharge stream" may refer to a stream after being heated by passing the bottom stream through the reboiler, the heat exchanger, and the like.

In the present invention, the term "side stream" may refer to a stream discharged from a middle stage of the distillation column, before heated using a side reboiler, the heat exchanger, and the like.

In the present invention the term "C# hydrocarbon", wherein is a positive integer, represents all hydrocarbons having # carbon atoms. Therefore, the term "C8 hydrocarbon" represents a hydrocarbon compound having 8 carbon atoms. In addition, the term "C#+ hydrocarbon" represents all hydrocarbon molecules having # or more carbon atoms. Therefore, the term "C9+ hydrocarbon" represents a mixture of hydrocarbons having 9 or more carbon atoms. In addition, the term "C#− hydrocarbon" represents all hydrocarbon molecules having # or fewer carbon atoms. Therefore, the term "C7− hydrocarbon" represents a mixture of hydrocarbons having 7 or fewer carbon atoms.

In the present invention, BTX is an abbreviation of benzene, toluene, and xylene, and the xylene may include ethylene benzene, m-xylene, o-xylene, and p-xylene.

Hereinafter, the present invention will be described in more detail for better understanding of the present invention.

An exemplary embodiment is directed to a method of producing aromatic hydrocarbons. The method of producing aromatic hydrocarbons produces BTX and styrene at the same time by one process, and the process may be simplified and process energy may be reduced as compared with the conventional method of producing BTX and styrene separately.

Specifically, the conventional BTX production process was performed by largely including a gasoline hydrogenation (GHT) process, a prefraction (PF) process, and an extractive distillation process (EDP). In this case, the total amount of the raw material stream is supplied to gasoline hydrogenation (GHT), thereby increasing an amount of hydrogen used due to an increase in a flow rate supplied to the gasoline hydrogenation (GHT). In addition, the prefraction (PF) process for separating benzene, toluene, and xylene has be performed after the gasoline hydrogenation (GHT) process, which complicates the process, and in particular, in the case of xylene, since the route for producing xylene from C8+ hydrocarbons remaining after separating prefractionated C8+ hydrocarbons, benzene, and toluene is long, the process is more complicated.

In addition, the conventional styrene extractive distillation process is a process of directly producing styrene from RPG through an extractive distillation process (EDP), and may be positioned in a front end of the BTX production process. A prefraction step of RPG to C7− hydrocarbons, a C8 hydrocarbon, and C9+ hydrocarbons is performed beforehand to separate a C8 hydrocarbon abundant in styrene before supplying the RPG to the extractive distillation process. However, since separated C7− hydrocarbons and a C8 hydrocarbon has to be introduced into the BTX production process and subjected to a gasoline hydrogenation process, they are mixed again. After performing the gasoline hydrogenation process step, the C7− hydrocarbons and the C8 hydrocarbon are separated again in the BTX production process, and as such, performing a step of separating the C7− hydrocarbons and the C8 hydrocarbon twice leads to a waste of process costs and energy.

As such, conventionally, RPG was used to produce BTX and styrene in separate processes. In this case, there were problems such as occurrence of unnecessary process steps and excessive energy consumption as described above.

Regarding this, in the present invention, a process capable of producing BTX and styrene at the same time, which may not be technically derived from each conventional process for producing BTX and styrene individually, was designed, and the process was further simplified and output of BTX and styrene relative to an amount of a raw material used was increased to the maximum while minimizing a process energy use.

According to an exemplary embodiment of the present invention, the method of producing aromatic hydrocarbons may be described with reference to FIG. 1. A method of producing aromatic hydrocarbons according to an exemplary embodiment includes: a step of supplying a raw material stream to a C6 separation column (DeC6), supplying an upper discharge stream from the C6 separation column (DeC6) to a first gasoline hydrogenation unit ($1^{st}$ GHT), and supplying a lower discharge stream from the C6 separation column to a C7 separation column (DeC7); a step of supplying an upper discharge stream from the C7 separation column (DeC7) to the first gasoline hydrogenation unit ($1^{st}$ GHT) and supplying a lower discharge stream from the C7 separation column to a C8 separation column (DeC8); a step of separating benzene and toluene from a discharge stream from the first gasoline hydrogenation unit ($1^{st}$ GHT); a step of removing a lower discharge stream from the C8 separation column (DeC8) and supplying an upper discharge stream from the C8 separation column to a second extractive distillation column ($2^{nd}$ EDC); and a step of separating styrene from a lower discharge stream from the second extractive distillation column ($2^{nd}$ EDC) and separating xylene from an upper discharge stream from the second extractive distillation column, wherein an overhead stream of the C8 separation column (DeC8) is condensed by heat exchange with one or more streams in the process in one or more heat exchangers and then is supplied to the second extractive distillation column ($2^{nd}$ EDC) as the upper discharge stream from the C8 separation column (DeC8).

According to an exemplary embodiment of the present invention, the raw material stream may include raw pyrolysis gasoline (RPG). The raw pyrolysis gasoline may be a by-product of a process producing ethylene, propylene, and the like using naphtha in a unit forming a naphtha cracking center (NCC). The RPG as the raw material stream may be a C5+ hydrocarbon mixture, specifically a mixture abundant in C5 hydrocarbons to C10 hydrocarbons. For example, the RPG may include one or more selected from the group consisting of iso-pentane, n-pentane, 1,4-pentadiene, dimethyl acetylene, 1-pentene, 3-methyl-1-butene, 2-methyl-1-butene, 2-methyl-2-butene, isoprene, trans-2-pentene, cis-2-pentene, trans-1,3-pentadiene, cyclopentadiene, cyclopentane, cyclopentene, n-hexane, cyclohexane, 1,3-cyclohexadiene, n-heptane, 2-methylhexane, 3-methylhexane, n-octane, n-nonane, benzene, toluene, ethylbenzene, m-xylene, o-xylene, p-xylene, styrene, dicyclopentadiene, indene, and indane.

According to an exemplary embodiment of the present invention, a temperature of the raw material stream may be 15° C. to 60° C., 20° C. to 50° C., or 30° C. to 50° C.

According to an exemplary embodiment of the present invention, the raw material stream was separated into C7− hydrocarbons and C8+ hydrocarbons to efficiently produce BTX and styrene from the raw material stream including C5 hydrocarbons to C10 hydrocarbons. Here, the stream including C7− hydrocarbons may be a stream for producing benzene and toluene and the stream including C8+ hydrocarbons may be a stream for producing styrene and xylene.

According to an exemplary embodiment of the present invention, a C6 separation column (DeC6) and a C7 separation column (DeC7) were provided to separate the raw material stream into C7− hydrocarbons and C8+ hydrocarbons. Specifically, the raw material stream was supplied to the C6 separation column (DeC6), an upper discharge stream including C6− hydrocarbons in the C6 separation column (DeC6) was supplied to the first gasoline hydrogenation unit, and a lower discharge stream including C7+ hydrocarbons was supplied to the C7 separation column (DeC7). In addition, in the C7 separation column (DeC7), an upper discharge stream including a C7 hydrocarbon and a lower discharge stream including C8+ hydrocarbons were separated, the upper discharge stream including a C7 hydrocarbon was supplied to the first gasoline hydrogenation unit ($1^{st}$ GHT), and the lower discharge stream including C8+ hydrocarbons was supplied to a C8 separation column (DeC8). Here, the upper discharge stream from the C6 separation column (DeC6) and the upper discharge stream from the C7 separation column (DeC7) may be supplied to the first gasoline hydrogenation unit ($1^{st}$ GHT) as individual streams, or may be supplied to the first gasoline hydrogenation unit ($1^{st}$ GHT) as a mixed stream which is mixed in an arbitrary area. As such, the C6 separation column (DeC6) and the C7 separation column (DeC7) may be operated at a relatively low temperature, and thus, a lower portion temperature of each column is lowered to suppress production of an oligomer and a polymer and suppress fouling production in the reboiler installed in the lower portion of each column. In addition, by using a low-grade heat source as a heat source of the reboiler installed in the lower portion of each column, an energy saving effect may be achieved, and cooling water at a relatively high temperature may be used in the condenser installed in the upper portion of each column.

According to an exemplary embodiment of the present invention, an operation pressure of the C6 separation column (DeC6) may be 250 mmHg to 800 mmHg, 300 mmHg to 700 mmHg, or 300 mmHg to 600 mmHg, and an operation temperature thereof may be 30° C. to 140° C., 30° C. to 130° C., or 30° C. to 120° C. By operating the C6 separation column (DeC6) at the temperature and pressure in the above ranges, the upper discharge stream including C6− hydrocarbons and the lower discharge stream including C7+ hydrocarbons may be separated and activity in the lower portion may be inhibited to prevent a side reaction. Here, the temperature of the lower discharge stream from the C6 separation column (DeC6) may be 80° C. to 140° C., 80° C. to 130° C., or 80° C. to 120° C. In addition, the temperature of a side stream from the C6 separation column (DeC6) may be 70° C. to 105° C., 70° C. to 95° C., or 70° C. to 90° C.

According to an exemplary embodiment of the present invention, an operation pressure of the C7 separation column (DeC7) may be 40 mmHg to 300 mmHg, 50 mmHg to 250 mmHg, or 50 mmHg to 220 mmHg, and an operation temperature thereof may be 30° C. to 150° C., 30° C. to 140° C., or 30° C. to 130° C. By operating the C7 separation column (DeC7) at the temperature and pressure in the above ranges, the upper discharge stream including a C7 hydrocarbon and the lower discharge stream including C8+ hydrocarbons may be separated and activity in the lower portion may be inhibited to prevent a side reaction.

The raw material stream may be separated into a stream including C7− hydrocarbons and a stream including C8+ hydrocarbons by passing through the C6 separation column (DeC6) and the C7 separation column (DeC7), and the stream including C7− hydrocarbons may be supplied to the first gasoline hydrogenation unit ($1^{st}$ GHT) for producing benzene and toluene and the stream including C8+ hydrocarbons may be supplied to the C8 separation column (DeC8) for producing styrene and xylene.

According to an exemplary embodiment of the present invention, a C6 separation column used in the prefraction step in the conventional BTX production process may be reused as the C6 separation column (DeC6).

According to an exemplary embodiment of the present invention, the upper discharge stream from each of the C6 separation column (DeC6) and the C7 separation column (DeC7) may be supplied to the first gasoline hydrogenation unit ($1^{st}$ GHT) and subjected to a hydrodesulfurization process in the presence of separately supplied hydrogen and catalyst. The catalyst may be a catalyst allowing selective hydrogenation. For example, the catalyst may include one or more selected from the group consisting of palladium, platinum, copper, and nickel. In some cases, the catalyst may be supported on one or more supporters selected from the group consisting of gamma alumina, activated carbon, and zeolite, and then used.

According to an exemplary embodiment of the present invention, benzene and toluene may be separated and produced from the first gasoline hydrogenation unit ($1^{st}$ GHT). Specifically, the discharge stream from the first gasoline hydrogenation unit ($1^{st}$ GHT) is supplied to the first extractive distillation column ($1^{st}$ EDC), and benzene and toluene may be separated from the lower discharge stream from the first extractive distillation column ($1^{st}$ EDC).

More specifically, the first gasoline hydrogenation unit ($1^{st}$ GHT) may include the first gasoline hydrogenation reactor and the second gasoline hydrogenation reactor, the upper discharge streams from the C6 separation column (DeC6) and the C7 separation column (DeC7) are supplied to the first gasoline hydrogenation reactor, the discharge stream from the first gasoline hydrogenation reactor is supplied to the second gasoline hydrogenation reactor, a discharge stream from the second gasoline hydrogenation reactor is supplied to the first extractive distillation column ($1^{st}$ EDC), and benzene and toluene may be separated from the lower discharge stream from the first extractive distillation column ($1^{st}$ EDC). Here, the discharge stream from the second gasoline hydrogenation reactor may be passed through a stripper and then supplied to the first extractive distillation column ($1^{st}$ EDC).

In addition, the first gasoline hydrogenation unit ($1^{st}$ GHT) may further include a separately required device in addition to the first gasoline hydrogenation reactor and the second gasoline hydrogenation reactor. For example, the first gasoline hydrogenation unit ($1^{st}$ GHT) may further include a C5 separation column and the C5 separation column may be disposed between the first gasoline hydrogenation reactor and the second gasoline hydrogenation reactor. Thus, the upper discharge stream from the C6 separation column (DeC6) and the C7 separation column (DeC7) is subjected to the first gasoline hydrogenation unit ($1^{st}$ GHT), while impurities such as a fuel gas (F/G) and C5 hydrocarbons may be removed from the upper discharge stream from the C6 separation column (DeC6) and the C7 separation column (DeC7).

An operation temperature of the first gasoline hydrogenation reactor may be 50° C. to 200° C., 60° C. to 170° C., or 60° C. to 140° C. The first gasoline hydrogenation reactor is operated at a temperature in the above ranges, thereby performing the hydrogenation reaction in a liquid phase. Specifically, in the first gasoline hydrogenation reactor, the hydrogenation reaction may be performed in a liquid phase at a low temperature for removing olefins. For example, the olefin is a hydrocarbon having a double bond, and may include styrene and diolefin. The double bond may be broken by the hydrogenation reaction in the first gasoline hydrogenation reactor to convert the olefin into a saturated hydrocarbon.

An operation temperature of the second gasoline hydrogenation reactor may be 250° C. to 400° C., 280° C. to 360° C., or 280° C. to 320° C. The second gasoline hydrogenation reactor is operated at a temperature in the above ranges, thereby performing the hydrogenation reaction in a gas phase. Specifically, residual olefins not been removed in the first gasoline hydrogenation reactor are removed in the second gasoline hydrogenation reactor, and the hydrogenation reaction may be performed in a gas phase for removing sulfur. Thus, the discharge stream from the second gasoline hydrogenation reactor from which olefins and sulfur have been removed may be passed through a stripper without additional prefraction and a total amount of the same then supplied to the first extractive distillation column ($1^{st}$ EDC).

Specifically, in the conventional BTX production process, a total amount of the raw material stream is subjected to the hydrodesulfurization reaction, and in order to separate benzene, toluene, and xylene therefrom, columns for a prefraction process and a xylene separation column (MX) are required, and even in the case of theoretically combining the conventional BTX production process and a styrene extractive distillation process, it is impossible to remove the prefraction columns and the xylene separation column (MX). However, in the present invention, only the upper discharge stream from the C6 separation column (DeC6) and the upper discharge stream from the C7 separation column (DeC7), that is, the streams including C7– hydrocarbons are subjected to the first gasoline hydrogenation unit ($1^{st}$ GHT) and do not require separate prefraction, and due to the second gasoline hydrogenation unit ($2^{nd}$ GHT) described later, a xylene separation column (MX) is also not required.

According to an exemplary embodiment of the present invention, the raw material stream including C5 and C6 hydrocarbons may be separately supplied to the first gasoline hydrogenation unit ($1^{st}$ GHT). Here, the raw material stream supplied to the first gasoline hydrogenation unit ($1^{st}$ GHT) may not include styrene. For example, the raw material stream including C5 and C6 hydrocarbons separately supplied to the gasoline hydrogenation unit ($1^{st}$ GHT) may include one or more selected from the group consisting of cyclopentadiene, pentadiene, isoprene, cyclopentene, 1-pentene, 3-methyl-1-butene, cyclopentane, 2-methylbutene, normal pentane, benzene, and C6 non-aromatic hydrocarbons, from the lower discharge stream from a C4 separation column (not shown) in an NCC process. Conventionally, the lower discharge stream from the C4 separation column was mixed with RPG described above and used as the raw material stream of a BTX production process and a styrene production process. However, the lower discharge stream from the C4 separation column includes benzene but does not include styrene, and thus, when supplied to the C6 separation column (DeC6), an additional process such as unnecessary separation and mixing is performed in the conventional process. Thus, in the present invention, the lower discharge stream from the C4 separation column (not shown) is separately supplied to the first gasoline hydrogenation unit ($1^{st}$ GHT) to decrease the flow rate supplied to the C6 separation column (DeC6) and is not subjected to an unnecessary process step to reduce energy.

A content of olefins in the raw material stream separately supplied to the first gasoline hydrogenation unit ($1^{st}$ GHT) may be 40 wt % or more, 40 wt % to 70 wt %, or 40 wt % to 60 wt %.

According to an exemplary embodiment of the present invention, the stream discharged from the first gasoline hydrogenation unit ($1^{st}$ GHT) may include a C6 aromatic hydrocarbon and a C7 aromatic hydrocarbon. As a specific example, the discharge stream from the first gasoline hydrogenation unit ($1^{st}$ GHT) may be a stream abundant in benzene and toluene, and this may be supplied to the first extractive distillation column ($1^{st}$ EDC) and subjected to an extraction process.

In the first extractive distillation column ($1^{st}$ EDC), an extraction solvent may be used to separate and produce benzene and toluene from the discharge stream from the first gasoline hydrogenation unit ($1^{st}$ GHT). For example, the extraction solvent may include one or more selected from the group consisting of sulfolane, alkyl-sulfolane, N-formyl morpholine, N-methyl pyrrolidone, tetraethylene glycol, triethylene glycol, and diethylene glycol. In addition, the extraction solvent may further include water as a co-solvent.

In the first extractive distillation column ($1^{st}$ EDC), the extraction solvent may be used to separate an aromatic hydrocarbon and a non-aromatic (Non Aro) hydrocarbon in the discharge stream from the first gasoline hydrogenation unit ($1^{st}$ GHT). Specifically, in the first extractive distillation column ($1^{st}$ EDC), an aromatic hydrocarbon in the discharge stream from the first gasoline hydrogenation unit ($1^{st}$ GHT) may be selectively extracted and discharged to the lower portion of the first extractive distillation column ($1^{st}$ EDC), and a non-aromatic hydrocarbon may be separated from the upper portion of the first extractive distillation column ($1^{st}$ EDC).

A separately required device may be further included in the rear end of the first extractive distillation column ($1^{st}$ EDC). For example, the lower discharge stream from the first extractive distillation column (1$^{st}$ EDC) may include the extraction solvent together with the aromatic hydrocarbons as an extract. Therefore, the lower discharge stream from the first extractive distillation column (1$^{st}$ EDC) is subjected to a separate solvent recovery column to be separated into the extraction solvent and the aromatic hydrocarbons.

The lower discharge stream from the first extractive distillation column (1$^{st}$ EDC), for example, the lower discharge stream from the first extractive distillation column (1$^{st}$ EDC) including the aromatic hydrocarbon passed through a solvent recovery column and separated, is then passed through one or more benzene separation columns and a toluene separation column (TOL), whereby benzene and toluene may be separated from the lower discharge stream from the first extractive distillation column (1$^{st}$ EDC). For example, the lower discharge stream from the first extractive distillation column (1$^{st}$ EDC) may be supplied to a benzene separation column (BZ) to separate benzene from an upper portion of the benzene separation column (BZ), the lower discharge stream from the benzene separation column (BZ) may be supplied to the toluene separation column (TOL) to separate toluene (TOL) from an upper portion, and a remaining trace amount of C8+ hydrocarbon heavy materials may be discharged from the lower portion.

According to an exemplary embodiment of the present invention, the lower discharge stream from the C7 separation column (DeC7) may be supplied to the C8 separation column (DeC8) as a stream including C8+ hydrocarbons, and may be separated into an upper discharge stream including a C8 hydrocarbon and a lower discharge stream including C9+ hydrocarbons in the C8 separation column (DeC8). Here, the stream including C9+ hydrocarbons may be removed by being discharged from the C8 separation column (DeC8) to the outside to remove an unnecessary process in which components which are not required in the BTX production process are hydrodesulfurized and removed after separation.

According to an exemplary embodiment of the present invention, the upper discharge stream from the C8 separation column (DeC8) including C8+ hydrocarbons may be supplied to the second extractive distillation column (2$^{nd}$ EDC) and subjected to an extraction process.

According to an exemplary embodiment of the present invention, an operation pressure of the C8 separation column (DeC8) may be 100 mmHg to 350 mmHg, 130 mmHg to 330 mmHg, or 150 mmHg to 300 mmHg. By operating the C8 separation column (DeC8) at the pressure in the above ranges, the overhead stream of the C8 separation column (DeC8) may be used to perform heat exchange through one or more streams in the process and one or more heat exchangers. Specifically, condensation heat of the overhead stream of the C8 separation column (DeC8) to be discarded as waste heat is reused to heat another stream in the process, thereby reducing process energy. For example, the overhead stream of the C8 separation column (DeC8) may exchange heat with any one or more streams of the raw material stream, a bottom stream of the C6 separation column (DeC6), and a side stream of the C6 separation column (DeC6) in one or more heat exchangers. In this case, the condensation heat of the overhead stream of the C8 separation column (DeC8) is used to preheat the raw material stream or heat the bottom stream of the C6 separation column (DeC6) and the side stream of the C6 separation column (DeC6), and the overhead stream of the C8 separation column (DeC8) may be condensed.

In the present invention, the C8 separation column (DeC8) is operated at a pressure of 100 mmHg to 350 mmHg, thereby controlling a temperature of the overhead stream of the C8 separation column (DeC8) to a temperature range allowing heat exchange with another stream in the process, while minimizing an increase in side reactions due to activity in the lower portion of the C8 separation column (DeC8). Specifically, a temperature difference between streams which exchange heat with each other is needed for heat exchange, and the temperature of the overhead stream of the C8 separation column (DeC8) may have a temperature range to allow heat exchange with the raw material stream, the bottom stream of the C6 separation column (DeC6), and the side stream of the C6 separation column (DeC6).

Figure 2:
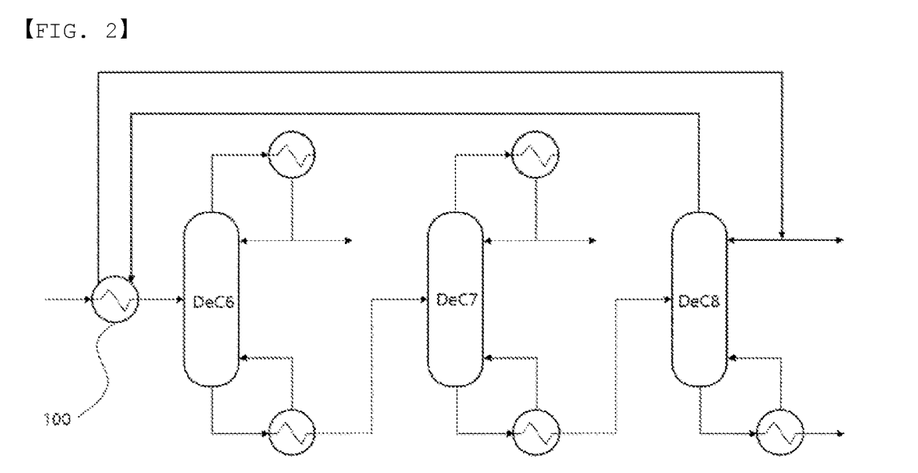
FIGS. 2 to 5 are flow charts of a heat exchange process of the method of producing aromatic hydrocarbons according to each Example of the present invention, respectively.
Figure 3:
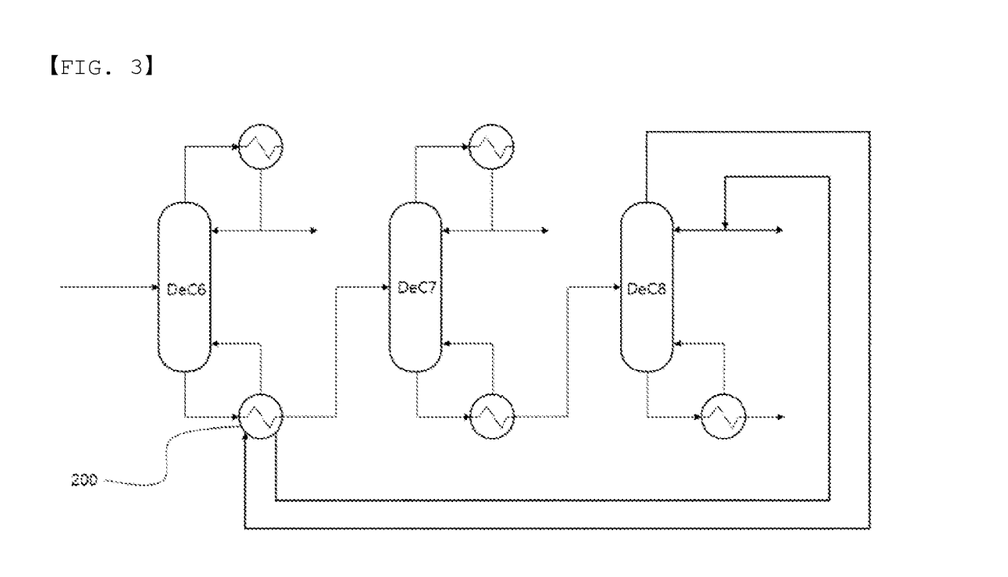
Figure 4:
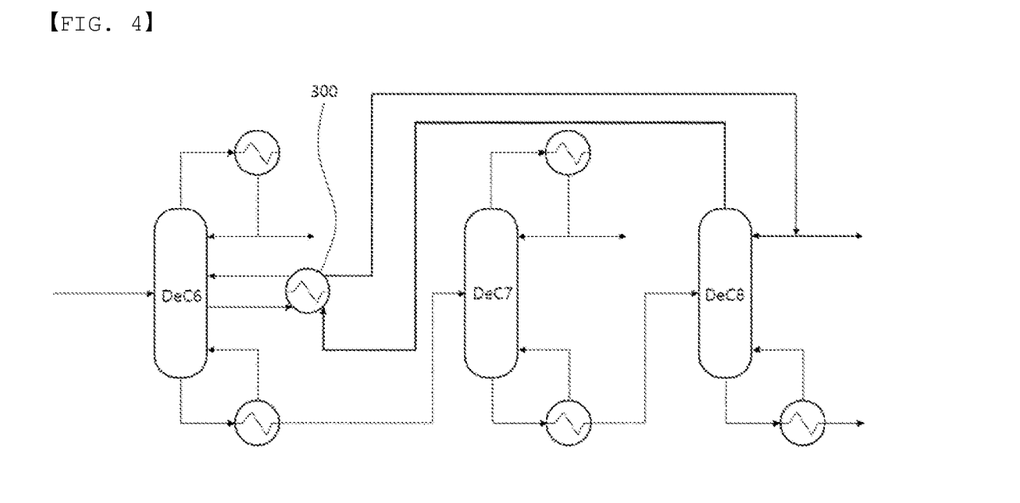

According to an exemplary embodiment of the present invention, the overhead stream of the C8 separation column (DeC8) may be supplied to a first heat exchanger 100 and exchange heat with the raw material stream in the first heat exchanger 100, may be supplied to a second heat exchanger 200 and exchange heat with the bottom stream of the C6 separation column (DeC6) in the second heat exchanger 200, or may be supplied to a third heat exchanger 300 and exchange heat with the side stream of the C6 separation column (DeC6) in the third heat exchanger 300. Specifically, when the overhead stream of the C8 separation column (DeC8) is supplied to the first heat exchanger 100 and exchanges heat with the raw material stream in the first heat exchanger 100, the raw material stream may be preheated and supplied to the C6 separation column (DeC6) to decrease an amount of the heat source used for heating the raw material stream in the C6 separation column (DeC6). In addition, when the overhead stream of the C8 separation column (DeC8) is supplied to the second heat exchanger 200 and exchanges heat with the bottom stream of the C6 separation column (DeC6) in the second heat exchanger 200, an amount of steam used in the reboiler of the C6 separation column (DeC6) may be significantly decreased or the reboiler may be replaced with the second heat exchanger 200. In addition, when the overhead stream of the C8 separation column (DeC8) is supplied to the third heat exchanger 300 and exchanges heat with the side stream of the C6 separation column (DeC6) in the third heat exchanger 300, the side stream of the C6 separation column (DeC6) may be heated and then circulated to supply the heat source to a middle stage of the C6 separation column (DeC6), thereby significantly decreasing an amount of steam used in the reboiler of the C6 separation column (DeC6).

According to an exemplary embodiment of the present invention, the overhead stream of the C8 separation column (DeC8) may be divided and input to any one or more heat exchangers of the first heat exchanger 100, the second heat exchanger 200, and the third heat exchanger 300 and exchange heat with any one or more streams of the raw material stream, the bottom stream of the C6 separation column (DeC6), and the side stream of the C6 separation column (DeC6).

Figure 5:
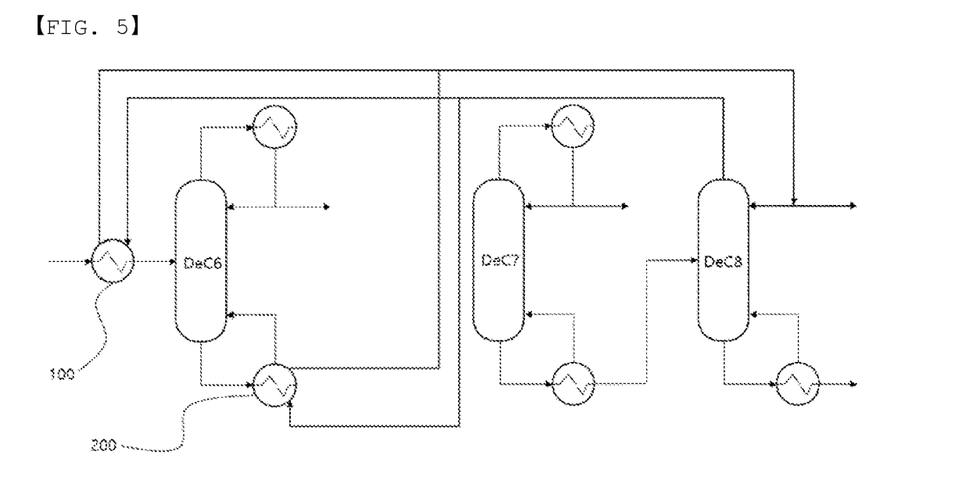

According to an exemplary embodiment of the present invention, the overhead stream of the C8 separation column (DeC8) is divided and input to the first heat exchanger 100 and the second heat exchanger 200, and exchanges heat with the raw material stream and the bottom stream of the C6 separation column (DeC6).

According to an exemplary embodiment of the present invention, when the overhead stream of the C8 separation column (DeC8) is divided and input to two or more heat exchangers of the first heat exchanger 100, the second heat exchanger 200, and the third heat exchanger 300, the plurality of heat exchangers may be configured without limitation in a series arrangement, a parallel arrangement, or a mixed arrangement of series and parallel. In addition, the order of the plurality of heat exchangers may be freely changed as necessary.

According to an exemplary embodiment of the present invention, after the overhead stream of the C8 separation column (DeC8) is condensed by heat exchange in one or more heat exchangers, a part of the condensed upper discharge stream from the C8 separation column (DeC8) may be refluxed to the C8 separation column (DeC8) and the remaining stream may be supplied to the second extractive distillation column ($2^{nd}$ EDC). Here, the overhead stream of the C8 separation column (DeC8) exchanges heat with one or more streams in the process, whereby a separate condenser in the upper portion of the C8 separation column (DeC8) is not required. Otherwise, if necessary, the overhead stream of the C8 separation column (DeC8) which has exchanged heat by the heat exchanger may be further condensed by having a separate condenser, a part of the condensed upper discharge stream from the C8 separation column (DeC8) which has been condensed by the heat exchanger and a separate condenser may be refluxed to the C8 separation column (DeC8), and the remaining stream may be supplied to the second extractive distillation column ($2^{nd}$ EDC).

According to an exemplary embodiment of the present invention, in the second extractive distillation column ($2^{nd}$ EDC), aromatic hydrocarbons and vinyl aromatic hydrocarbons may be separated from the upper discharge stream of the C8 separation column (DeC8) using the extraction solvent. Specifically, the C8 vinyl aromatic hydrocarbon abundant in styrene in the upper discharge stream from the C8 separation column (DeC8) may be selectively extracted in the second extractive distillation column ($2^{nd}$ EDC) to be separated as the lower portion of the second extractive distillation column ($2^{nd}$ EDC), and the C8 aromatic hydrocarbon abundant in xylene may be separated as the upper portion of the second extractive distillation column ($2^{nd}$ EDC). Here, the extraction solvent may include, for example, one or more selected from the group consisting of sulfolane, alkyl-sulfolane, N-formyl morpholine, N-methyl pyrrolidone, tetraethylene glycol, triethylene glycol, and diethylene glycol. In addition, the extraction solvent may further include water as a co-solvent.

Styrene may be separated from the lower discharge stream and xylene may be separated from the upper discharge stream from the second extractive distillation column ($2^{nd}$ EDC), respectively.

A separately required device may be further included in the rear end of the second extractive distillation column ($2^{nd}$ EDC). For example, the lower discharge stream from the second extractive distillation column ($2^{nd}$ EDC) may include the extraction solvent together with the C8 vinyl aromatic hydrocarbon as an extract. Therefore, the lower discharge stream from the second extractive distillation column ($2^{nd}$ EDC) may be subjected to a separate solvent recovery column to be separated into the extraction solvent and the C8 vinyl aromatic hydrocarbon, thereby separating the C8 vinyl aromatic hydrocarbon, that is, styrene.

The upper discharge stream from the second extractive distillation column ($2^{nd}$ EDC) is a stream including a C8 aromatic hydrocarbon abundant in xylene, and may be subjected to the second gasoline hydrogenation unit ($2^{nd}$ GHT) to produce xylene. Specifically, in the second gasoline hydrogenation unit ($2^{nd}$ GHT), olefins and sulfur remaining in the upper discharge stream from the second extractive distillation column ($2^{nd}$ EDC) may be hydrogenated and removed, and xylene (MX) may be directly produced from the upper discharge stream from the second extractive distillation column ($2^{nd}$ EDC) which has passed through the second gasoline hydrogenation unit ($2^{nd}$ GHT).

Hydrogen and a catalyst are separately supplied to the second gasoline hydrogenation unit ($2^{nd}$ GHT), and a gasoline hydrogenation process step to achieve hydrodesulfurization in the presence of hydrogen and the catalyst may be performed. The catalyst may be a catalyst allowing selective hydrogenation. For example, the catalyst may include one or more selected from the group consisting of palladium, platinum, copper, and nickel. In some cases, the catalyst may be supported on one or more supporters selected from the group consisting of gamma alumina, activated carbon, and zeolite and then used.

The second gasoline hydrogenation unit ($2^{nd}$ GHT) does not include the two gasoline hydrogenation reactors and includes only a third gasoline hydrogenation reactor, unlike the first gasoline hydrogenation unit ($1^{st}$ GHT), thereby decreasing a plant size and minimizing energy use. Specifically, the upper discharge stream from the second extractive distillation column ($2^{nd}$ EDC) supplied to the third gasoline hydrogenation reactor includes a C8 aromatic hydrocarbon abundant in xylene and hardly contains olefins such as diolefin and styrene, thereby omitting a hydrogenation reaction to remove olefins by the liquid phase reaction at a low temperature. For example, the content of the olefins contained in the upper discharge stream from the second extractive distillation column ($2^{nd}$ EDC) may be 0.1 wt % or less or 0.01 wt % to 0.1 wt %.

Specifically, the upper discharge stream from the second extractive distillation column ($2^{nd}$ EDC) is supplied to the third gasoline hydrogenation reactor, and the hydrogenation reaction may progress at a temperature of 250° C. to 400° C., 280° C. to 360° C., or 280° C. to 320° C. in the third gasoline hydrogenation reactor. The third gasoline hydrogenation reactor is operated at a temperature in the above ranges, thereby performing the hydrogenation reaction in a gas phase. Specifically, in the third gasoline hydrogenation reactor, the olefins remaining in the upper discharge stream from the second extractive distillation column ($2^{nd}$ EDC) are removed, and the hydrogenation reaction may be performed in a gaseous phase to remove sulfur. Thus, a C8 aromatic hydrocarbon abundant in xylene from which olefins and sulfur are removed is discharged from the third gasoline hydrogenation reactor, and xylene (MX) may be produced without additional separation from the discharge stream from the third gasoline hydrogenation reactor.

However, even in the case in which the conventional BTX production process and styrene extractive distillation process are theoretically combined, the stream including a C8 aromatic hydrocarbon separated from the styrene extractive distillation process, that is, the upper discharge stream from the second extractive distillation column ($2^{nd}$ EDC) will be supplied to the first gasoline hydrogenation unit ($1^{st}$ GHT) together with the upper discharge stream from the C7 separation column (DeC7) as the raw material of the BTX production process. In this case, due to an increase of the flow rate supplied to the first gasoline hydrogenation unit ($1^{st}$ GHT), an amount of hydrogen used increases and a catalyst lifetime decreases. In addition, though the upper discharge stream from the second extractive distillation column ($2^{nd}$ EDC) includes a very small amount of olefins, it is subjected to both the first gasoline hydrogenation reactor and the second gasoline hydrogenation reactor like the first gasoline hydrogenation unit ($1^{st}$ GHT), resulting in unnecessary energy use. In addition, since the stream discharged from the first gasoline hydrogenation unit ($1^{st}$ GHT)

includes a C8 aromatic hydrocarbon together with a C6 aromatic hydrocarbon and a C7 aromatic hydrocarbon, a prefraction column for separating the C8 aromatic hydrocarbon and a xylene separation column (MX) is further required in a rear end of the discharge stream from the first gasoline hydrogenation unit ($1^{st}$ GHT).

According to an exemplary embodiment of the present invention, in the method of producing aromatic hydrocarbons, if necessary, devices such as a distillation column (not shown), a condenser (not shown), a reboiler (not shown), a valve (not shown), a pump (not shown), a separator (not shown), and a mixer (not shown) may be further installed.

The method of producing aromatic hydrocarbons according to the present invention has been described and illustrated in the drawings, but the description and the illustrations in the drawings are the description and the illustrations of only core constituents for understanding the present invention, and in addition to the process and apparatus described above and illustrated in the drawings, the process and the apparatus which are not described and illustrated separately may be appropriately applied and used for carrying out the method of producing aromatic hydrocarbons according to the present invention.

Hereinafter, the present invention will be described in more detail by the Examples. However, the following Examples are provided for illustrating the present invention. It would be apparent to a person skilled in the art that various modifications and alterations may be made without departing from the scope and spirit of the present invention, and the scope of the present invention is not limited thereto.

EXAMPLES

Example 1

Figure 1:
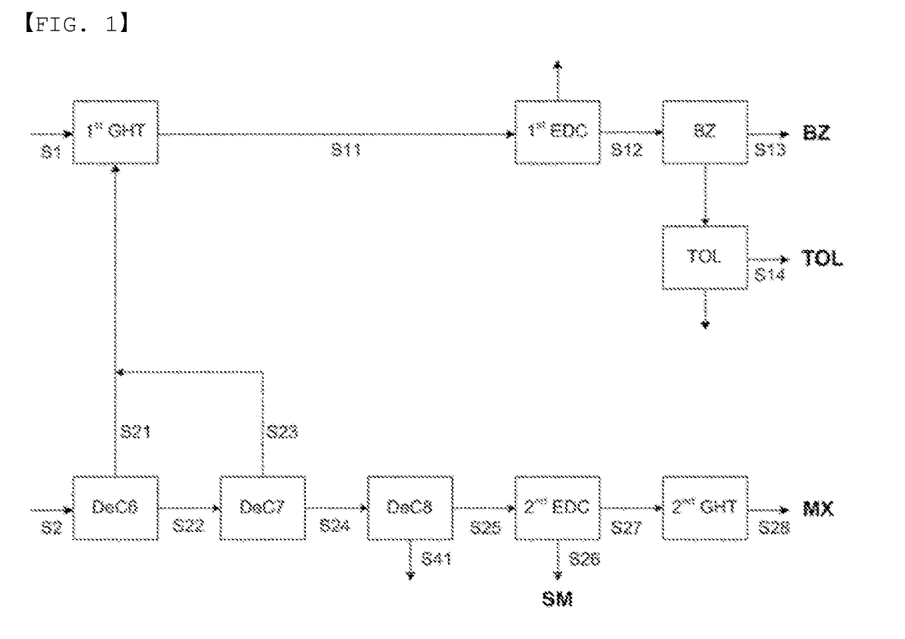
FIG. 1 is a process flow chart illustrating the method of producing aromatic hydrocarbons according to an exemplary embodiment of the present invention.

The process illustrated in FIG. 1 was simulated using an Aspen Plus simulator from Aspen Technology, Inc.

Specifically, a raw material stream including C5 to C10 hydrocarbons was supplied to a C6 separation column (DeC6) and a raw material stream including C5 and C6 hydrocarbons but no styrene was supplied to a first gasoline hydrogenation unit ($1^{st}$ GHT).

An upper discharge stream from the C6 separation column (DeC6) including C6− hydrocarbons was supplied to the first gasoline hydrogenation unit ($1^{st}$ GHT), and a lower discharge stream including C7+ hydrocarbons was supplied to a C7 separation column (DeC7). In addition, in the C7 separation column (DeC7), an upper discharge stream including a C7 hydrocarbon was supplied to the first gasoline hydrogenation unit ($1^{st}$ GHT), and a lower discharge stream including C8+ hydrocarbons was supplied to a C8 separation column (DeC8).

The upper discharge stream from the C6 separation column (DeC6) including C6− hydrocarbons and the upper discharge stream from the C7 separation column (DeC7) including a C7 hydrocarbon were supplied to the first gasoline hydrogenation unit ($1^{st}$ GHT), and a total amount of the discharge stream from the first gasoline hydrogenation unit ($1^{st}$ GHT) including the C6 aromatic hydrocarbon and the C7 aromatic hydrocarbon was supplied to the first extractive distillation column ($1^{st}$ EDC).

The lower discharge stream from the first extractive distillation column ($1^{st}$ EDC) included the C6 and C7 aromatic hydrocarbons, but was a stream from which non-aromatic hydrocarbons were removed, and was supplied to a benzene separation column (BZ), and benzene was separated from an upper portion of the benzene separation column (BZ) and the lower discharge stream was supplied to a toluene separation column (TOL). In the toluene separation column (TOL), toluene was separated from the upper portion and a heavy substance including C8+ hydrocarbons was separated from the lower portion and removed.

The lower discharge stream from the C7 separation column (DeC7) including the C8+ hydrocarbons was supplied to the C8 separation column (DeC8), the lower discharge stream including C9+ hydrocarbons was discharged from the C8 separation column (DeC8) to the outside and removed, and the upper discharge stream from the C8 separation column (DeC8) including a C8 hydrocarbon was supplied to the second extractive distillation column ($2^{nd}$ EDC). Here, the upper discharge stream from the C8 separation column (DeC8) was obtained by supplying the overhead stream of the C8 separation column (DeC8) to the first heat exchanger 100 and condensing the stream by heat exchange with the raw material stream, as illustrated in FIG. 2, and a part of the stream was refluxed to the C8 separation column (DeC8) and the remaining stream was supplied to the second extractive distillation column ($2^{nd}$ EDC). Here, if necessary, the raw material stream was further heated by supplying steam to a reboiler in the C6 separation column (DeC6), and the overhead stream of the C8 separation column (DeC8) exchanged heat in the first heat exchanger 100 and then was further cooled by a separate condenser (not shown).

The lower discharge stream from the second extractive distillation column ($2^{nd}$ EDC) included styrene and was supplied to a solvent recovery column to remove a solvent and then styrene was separated.

In addition, the upper discharge stream from the second extractive distillation column ($2^{nd}$ EDC) was a stream abundant in xylene and was supplied to a second gasoline hydrogenation unit ($2^{nd}$ GHT), and xylene was produced from the discharge stream from the second gasoline hydrogenation unit ($2^{nd}$ GHT).

A flow rate (ton/hr) of the stream depending on a process flow for the process simulation is listed in Table 1. In addition, a total amount of steam used in the process was measured as a total amount of energy used in the process, and is listed in Table 2, as a criterion (100.0) for a total amount of steam used in the other Examples and Comparative Examples.

Example 2

The process was performed in the same manner as in Example 1, except that the upper discharge stream from the C8 separation column (DeC8) was obtained by supplying the overhead stream of the C8 separation column (DeC8) to the second heat exchanger 200 and condensing the stream by heat exchange with the bottom stream of the C6 separation column (DeC6 6), as illustrated in FIG. 3, and a part of the stream was refluxed to the C8 separation column (DeC8) and the remaining stream was supplied to the second extractive distillation column ($2^{nd}$ EDC). Here, if necessary, the bottom stream of the C6 separation column (DeC6) was further heated by a separate reboiler (not shown) in addition to the second heat exchanger 200, and the overhead stream of the C8 separation column (DeC8) exchanged heat in the second heat exchanger 200 and then was further cooled by a separate condenser (not shown).

A flow rate (ton/hr) of the stream depending on a process flow of the process simulation is listed in Table 1. In addition, a total amount of steam used in the process was measured as a total amount of energy used in the process, and is shown in Table 2, as a relative amount to 100.0 of the amount of steam used measured in Example 1.

Example 3

The process was performed in the same manner as in Example 1, except that the upper discharge stream from the C8 separation column (DeC8) was obtained by supplying the overhead stream of the C8 separation column (DeC8) to the third heat exchanger 300 and condensing the stream by heat exchange with the side stream of the C6 separation column (DeC6), as illustrated in FIG. 4, and a part of the stream was refluxed to the C8 separation column (DeC8) and the remaining stream was supplied to the second extractive distillation column ($2^{nd}$ EDC). Here, if necessary, further heating was performed by supplying steam to a reboiler in the C6 separation column (DeC6), and the overhead stream of the C8 separation column (DeC8) exchanged heat in the third heat exchanger 300 and then was further cooled by a separate condenser (not shown).

A flow rate (ton/hr) of the stream depending on a process flow of the process simulation is listed in Table 1. In addition, a total amount of steam used in the process was measured as a total amount of energy used in the process, and is listed in Table 2, as a relative amount to 100.0 of the amount of steam used measured in Example 1.

Example 4

The process was performed in the same manner as in Example 1, except that the upper discharge stream from the C8 separation column (DeC8) was obtained by dividing and supplying the overhead stream of the C8 separation column (DeC8) to the first heat exchanger 100 and the second heat exchanger 200 and exchanging heat with the raw material stream and the bottom stream of the C6 separation column (DeC6), respectively, as illustrated in FIG. 5, and a part of the stream was refluxed to the C8 separation column (DeC8) and the remaining stream was supplied to the second extractive distillation column ($2^{nd}$ EDC). Here, if necessary, further heating was performed by a separate reboiler (not shown) in the C6 separation column (DeC6), and the overhead stream of the C8 separation column (DeC8) exchanged heat in the first heat exchanger 100 and the second heat exchanger 200 and then was further cooled by a separate condenser (not shown).

A flow rate (ton/hr) of the stream depending on a process flow of the process situation is listed in Table 1. In addition, a total amount of steam used in the process was measured as a total amount of energy used in the process, and is listed in Table 2, as a relative amount to 100.0 of the amount of steam used measured in Example 1.

Comparative Examples

Comparative Example 1

Figure 6:
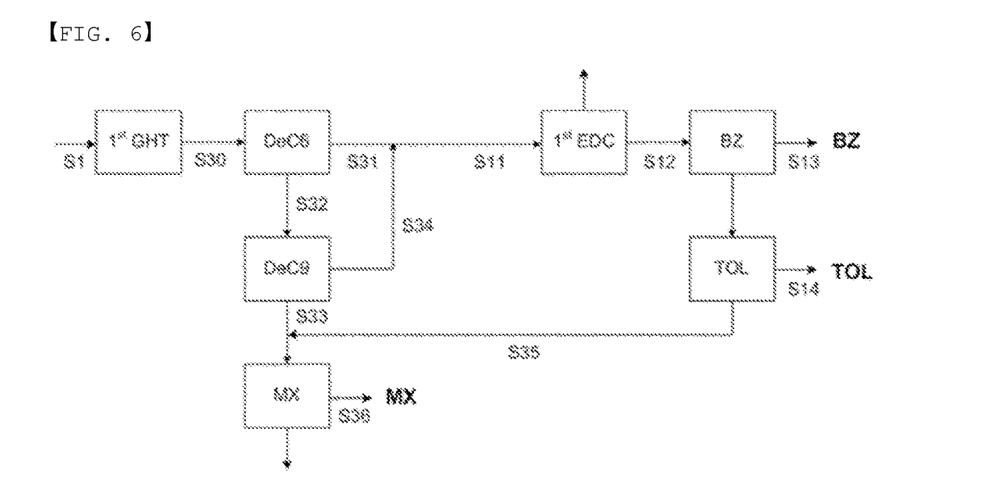
FIGS. 6 to 8 are process flow charts of the method of producing aromatic hydrocarbons according to each Comparative Example, respectively.

The process illustrated in FIG. 6 was simulated using an Aspen Plus simulator from Aspen Technology, Inc.

Specifically, a raw material stream including C5 to C10 hydrocarbons as the raw material stream was supplied to the first gasoline hydrogenation unit ($1^{st}$ GHT) and the discharge stream from the first gasoline hydrogenation unit ($1^{st}$ GHT) was supplied to the C6 separation column (DeC6). In the C6 separation column (DeC6), the upper discharge stream including a C6 aromatic hydrocarbon was supplied to the first extractive distillation column ($1^{st}$ EDC), and the lower discharge stream including C7+ aromatic hydrocarbons was supplied to a C9 separation column (DeC9).

In the C9 separation column (DeC9), the lower discharge stream including C8+ aromatic hydrocarbons was supplied to a xylene separation column (MX), and the stream including C7 and C8 aromatic hydrocarbons was supplied to the first extractive distillation column ($1^{st}$ EDC) together with the upper discharge stream from the C6 separation column (DeC6).

The lower discharge stream from the first extractive distillation column ($1^{st}$ EDC) included C6 to C8 aromatic hydrocarbons and was subjected to the benzene separation column (BZ) and the toluene separation column (TOL) to separate benzene and toluene, and the remaining stream was supplied to the xylene separation column (MX).

In the xylene separation column (MX), the lower discharge stream including C9+ hydrocarbons was removed and xylene was separated from the upper portion.

A flow rate (ton/hr) of the stream depending on a process flow of the process simulation is listed in Table 1.

Comparative Example 2

Figure 7:
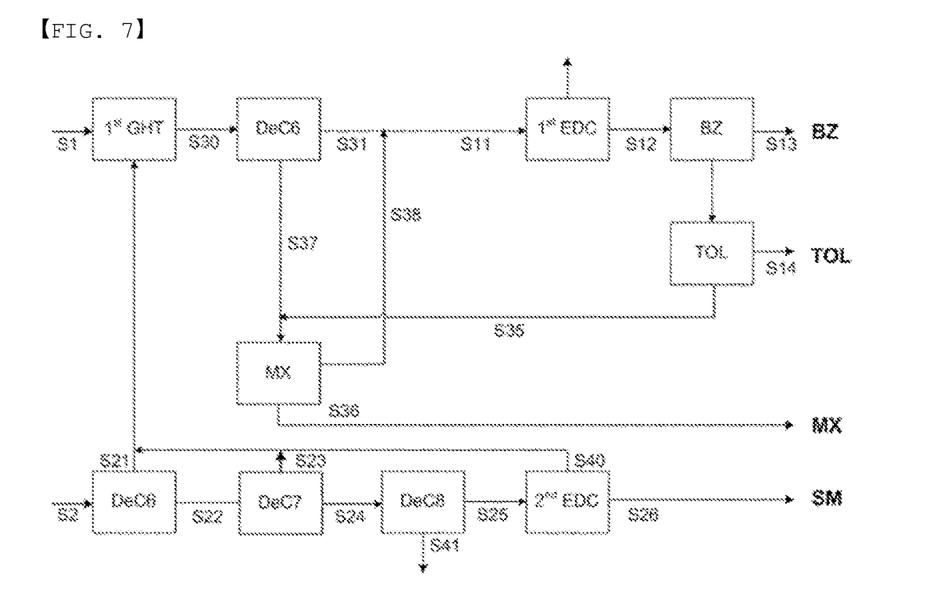

The process illustrated in FIG. 7 was simulated using an Aspen Plus simulator from Aspen Technology, Inc.

Specifically, a raw material stream including C5 to C10 hydrocarbons was supplied to the C6 separation column (DeC6) and a raw material stream including C5 and C6 hydrocarbons but no styrene was supplied to the first gasoline hydrogenation unit ($1^{st}$ GHT).

An upper discharge stream from the C6 separation column (DeC6) including C6− hydrocarbons was supplied to the first gasoline hydrogenation unit ($1^{st}$ GHT), and a lower discharge stream including C7+ hydrocarbons was supplied to a C7 separation column (DeC7). In addition, in the C7 separation column (DeC7), an upper discharge stream including a C7 hydrocarbon was supplied to the first gasoline hydrogenation unit ($1^{st}$ GHT), and a lower discharge stream including C8+ hydrocarbons was supplied to a C8 separation column (DeC8).

In the C8 separation column (DeC8), the lower discharge stream including C9+ hydrocarbons was discharged to the outside and removed, and the upper discharge stream from the C8 separation column (DeC8) including a C8 hydrocarbon was supplied to the second extractive distillation column ($2^{nd}$ EDC).

The lower discharge stream from the second extractive distillation column ($2^{nd}$ EDC) included styrene and was supplied to a solvent recovery column to remove a solvent and then styrene was separated.

The upper discharge stream from the second extractive distillation column ($2^{nd}$ EDC) included xylene, and was supplied to the first gasoline hydrogenation unit ($1^{st}$ GHT) together with the upper discharge streams from the C6 separation column (DeC6) and the C7 separation column (DeC7).

The discharge stream from the first gasoline hydrogenation unit ($1^{st}$ GHT) included C6 to C8 aromatic hydrocarbons and was supplied to the C6 separation column (DeC6). In the C6 separation column (DeC6), an upper discharge stream including a C6 aromatic hydrocarbon and a lower discharge stream including C7 and C8 aromatic hydrocarbons are divided, and the upper discharge stream from the C6 separation column (DeC6) was supplied to the first extractive distillation column ($1^{st}$ EDC) and the lower discharge stream was supplied to the xylene separation column (MX).

A lower discharge stream from the first extractive distillation column (1$^{st}$ EDC) was subjected to the benzene separation column (BZ) and the toluene separation column (TOL) to separate benzene and toluene, respectively, and the remaining stream was supplied to the xylene separation column (MX).

In the xylene separation column (MX), an upper discharge stream including a C7 aromatic hydrocarbon was supplied to the first extractive distillation column (1$^{st}$ EDC) with an upper discharge stream from the C6 separation column (DeC6), and xylene was produced from the lower discharge stream.

A flow rate (ton/hr) of the stream depending on a process flow of the process simulation is listed Table 1. In addition, a total amount of steam used in the process was measured as a total amount of energy used in the process according to each Example, and is listed in Table 2, as a relative amount to 100.0 of the amount of steam used measured in Example 1.

Comparative Example 3

Figure 8:
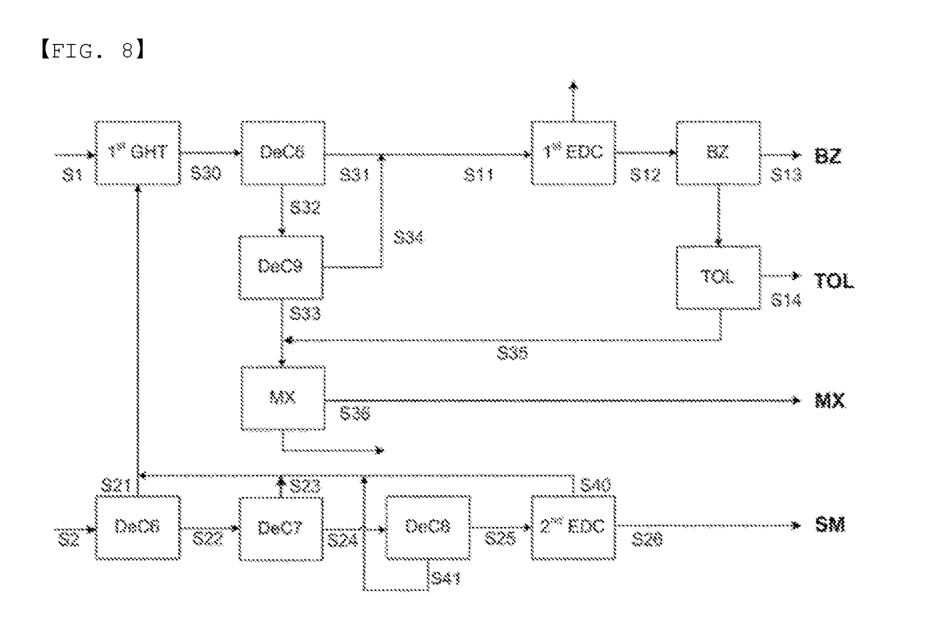

The process illustrated in FIG. 8 was simulated using an Aspen Plus simulator from Aspen Technology, Inc.

Specifically, the process was performed in the same manner as in Comparative Example 2, except that the lower discharge stream including C9+ hydrocarbons of the C8 separation column (DeC8) was supplied to the first gasoline hydrogenation unit (1$^{st}$ GHT) together with the upper discharge stream from the C6 separation column (DeC6), the upper discharge stream from the C7 separation column (DeC7), and the upper discharge stream from the second extractive distillation column (2$^{nd}$ EDC).

A flow rate (ton/hr) of the stream depending on a process flow of the process simulation is listed in Table 1. In addition, a total amount of steam used in the process was measured as a total amount of energy used in the process according to each Example, and is listed in Table 2, as a relative amount to 100.0 of the amount of steam used measured in Example 1.

Comparative Example 4

The process was performed in the same manner as in Example 1, except that the overhead stream of the C8 separation column (DeC8) was supplied to the first heat exchanger 100, did not exchange heat with the raw material stream, and was condensed by a separate condenser (not shown), and a part of the condensed upper discharge stream from the C8 separation column (DeC8) was refluxed and the remaining stream was supplied to the second extractive distillation column (2$^{nd}$ EDC). In addition, the raw material stream was heated by a separate heater (not shown).

A flow rate (ton/hr) of the stream depending on a process flow of the process simulation is listed in Table 1. In addition, a total amount of steam used in the process was measured as a total amount of energy used in the process according to each Example, and is listed in Table 2, as a relative amount to 100.0 of the amount of steam used measured in Example 1.

TABLE 1

|     | Example 1 | Example 2 | Example 3 | Example 4 | Comparative Example 1 | Comparative Example 2 | Comparative Example 3 | Comparative Example 4 |
|-----|-----------|-----------|-----------|-----------|-----------------------|-----------------------|-----------------------|-----------------------|
| S1  | 20.4      | 20.4      | 20.4      | 20.4      | 183.8                 | 20.4                  | 20.4                  | 20.4                  |
| S2  | 163.6     | 163.6     | 163.6     | 163.6     | N/A                   | 163.6                 | 163.6                 | 163.6                 |
| S11 | 119.4     | 119.4     | 119.4     | 119.4     | 119.8                 | 119.4                 | 119.4                 | 119.4                 |
| S12 | 88.4      | 88.4      | 88.4      | 88.4      | 89.6                  | 88.4                  | 88.4                  | 88.4                  |
| S13 | 64.6      | 64.6      | 64.6      | 64.6      | 64.6                  | 64.6                  | 64.6                  | 64.6                  |
| S14 | 23.4      | 23.4      | 23.4      | 23.4      | 23.4                  | 23.4                  | 23.4                  | 23.4                  |
| S21 | 60.0      | 60.0      | 60.0      | 60.0      | N/A                   | 60.0                  | 60.0                  | 60.0                  |
| S22 | 103.6     | 103.6     | 103.6     | 103.6     | N/A                   | 103.6                 | 103.6                 | 103.6                 |
| S23 | 61.6      | 61.6      | 61.6      | 61.6      | N/A                   | 61.6                  | 61.6                  | 61.6                  |
| S24 | 42.0      | 42.0      | 42.0      | 42.0      | N/A                   | 42.0                  | 42.0                  | 42.0                  |
| S25 | 19.4      | 19.4      | 19.4      | 19.4      | N/A                   | 19.4                  | 19.4                  | 19.4                  |
| S26 | 9.6       | 9.6       | 9.6       | 9.6       | N/A                   | 9.6                   | 9.6                   | 9.6                   |
| S27 | 9.6       | 9.6       | 9.6       | 9.6       | N/A                   | N/A                   | N/A                   | 9.6                   |
| S28 | 9.6       | 9.6       | 9.6       | 9.6       | N/A                   | N/A                   | N/A                   | 9.6                   |
| S30 | N/A       | N/A       | N/A       | N/A       | 161.4                 | 129.0                 | 151.6                 | N/A                   |
| S31 | N/A       | N/A       | N/A       | N/A       | 106.4                 | 113.4                 | 112.8                 | N/A                   |
| S32 | N/A       | N/A       | N/A       | N/A       | 55.0                  | N/A                   | 38.8                  | N/A                   |
| S33 | N/A       | N/A       | N/A       | N/A       | 41.6                  | N/A                   | 32.2                  | N/A                   |
| S34 | N/A       | N/A       | N/A       | N/A       | 13.4                  | N/A                   | 6.6                   | N/A                   |
| S35 | N/A       | N/A       | N/A       | N/A       | 1.6                   | 0.4                   | 0.4                   | N/A                   |
| S36 | N/A       | N/A       | N/A       | N/A       | 19.0                  | 10.0                  | 10.0                  | N/A                   |
| S37 | N/A       | N/A       | N/A       | N/A       | N/A                   | 15.6                  | N/A                   | N/A                   |
| S38 | N/A       | N/A       | N/A       | N/A       | N/A                   | 6.0                   | N/A                   | N/A                   |
| S40 | N/A       | N/A       | N/A       | N/A       | N/A                   | 9.6                   | 9.6                   | N/A                   |
| S41 | 22.6      | 22.6      | 22.6      | 22.6      | N/A                   | 22.6                  | 22.6                  | 22.6                  |

TABLE 2

|  | Example 1 | Example 2 | Example 3 | Example 4 | Comparative Example 2 | Comparative Example 3 | Comparative Example 4 |
|---|---|---|---|---|---|---|---|
| Total amount of steam used | 100.0 | 98.6 | 100.7 | 94.3 | 120.4 | 127.2 | 103.8 |

\* Total amount of steam used: Ratio of total amount of steam used relative to criterion (Example 1: 100.0)

As shown in Tables 1 and 2, in Examples 1 to 4 in which BTX and styrene are produced according to the method of the present invention, total output of benzene, toluene, xylene, and styrene were at an equal or superior level to that of the Comparative Examples.

In Examples 1 to 3, heat exchange of the overhead stream of the C8 separation column (DeC8) with one stream in the process was performed by one heat exchanger, thereby reducing the total amount of steam used in the process, as compared with Comparative Example 4 in which the same process was performed but heat exchange was not performed in the process. In particular, in Example 2 in which the overhead stream of the C8 separation column (DeC8) and the bottom stream of the C6 separation column (DeC6) were heat-exchanged, the heat exchange effect was the best.

In addition, in Example 4 in which the overhead stream of the C8 separation column (DeC8) and two streams in the process were heat-exchanged, the total amount of steam used in the process was 94.3 relative to Example 1 (100.0), which was the lowest.

In comparison, because styrene was not produced and only BTX was produced in Comparative Example 1, a comparison data for the total amount of steam used was not added. However, since the stream supplied to the first gasoline hydrogenation unit ($1^{st}$ GHT) was 183.8 ton/hr which was the largest amount, the amount of hydrogen used in the first gasoline hydrogenation unit ($1^{st}$ GHT) was significant and the catalyst lifetime was decreased, thereby increasing utility costs.

In addition, unlike the Examples in which the upper discharge stream separated from the second extractive distillation column ($2^{nd}$ EDC) was used to produce xylene, heat exchange between streams in the process was not performed in Comparative Example 2 and the upper discharge stream from the second extractive distillation column ($2^{nd}$ EDC) was input to the first gasoline hydrogenation unit ($1^{st}$ GHT), thereby increasing the stream supplied to the first gasoline hydrogenation unit ($1^{st}$ GHT) to increase the amount of hydrogen used and decrease the catalyst lifetime, resulting in an increase in utility costs. In addition, since a C8 hydrocarbon was introduced to the BTX production process, the C6 separation column (DeC6) and the xylene separation column (MX) for prefraction in the BTX production process were not removed to increase the amount of steam used.

In addition, in Comparative Example 3, even the lower discharge stream from the C8 separation column (DeC8) including C9+ hydrocarbons as well as the upper discharge stream from the second extractive distillation column ($2^{nd}$ EDC) was input to the first gasoline hydrogenation unit ($1^{st}$ GHT), thereby increasing the stream supplied to the first gasoline hydrogenation unit ($1^{st}$ GHT) to increase the amount of hydrogen used and decrease the catalyst lifetime, resulting in an increase in utility costs. In addition, since C8+ hydrocarbons were introduced to the BTX production process, the C6 separation column (DeC6), the C9 separation column (DeC9), and the xylene separation column (MX) for prefraction in the BTX production process were not removed to increase the amount of steam used.

The invention claimed is:

1. A method of producing aromatic hydrocarbons, the method comprising:

a step of supplying a raw material stream to a C6 separation column, supplying an upper discharge stream from the C6 separation column to a first gasoline hydrogenation unit, and supplying a lower discharge stream from the C6 separation column to a C7 separation column;

a step of supplying an upper discharge stream from the C7 separation column to the first gasoline hydrogenation unit and supplying a lower discharge stream from the C7 separation column to a C8 separation column;

a step of separating benzene and toluene from a discharge stream from the first gasoline hydrogenation unit;

a step of removing a lower discharge stream from the C8 separation column and supplying an upper discharge stream from the C8 separation column to a second extractive distillation column; and a step of separating styrene from a lower discharge stream from the second extractive distillation column and separating xylene from an upper discharge stream from the second extractive distillation column, wherein an overhead stream of the C8 separation column is condensed by heat exchange with one or more streams in the process in one or more heat exchangers and then supplied to the second extractive distillation column as the upper discharge stream from the C8 separation column.

2. The method of producing aromatic hydrocarbons of claim 1, wherein the overhead stream of the C8 separation column exchanges heat with any one or more streams of the raw material stream, a bottom stream of the C6 separation column, and a side stream of the C6 separation column in one or more heat exchangers.

3. The method of producing aromatic hydrocarbons of claim 1, wherein the overhead stream of the C8 separation column is supplied to a first heat exchanger and exchanges heat with the raw material stream in the first heat exchanger.

4. The method of producing aromatic hydrocarbons of claim 1, wherein the overhead stream of the C8 separation column is supplied to a second heat exchanger and exchanges heat in the second heat exchanger with the bottom stream of the C6 separation column.

5. The method of producing aromatic hydrocarbons of claim 1, wherein the overhead stream of the C8 separation column is supplied to a third heat exchanger and exchanges heat with the side stream of the C6 separation column in the third heat exchanger.

6. The method of producing aromatic hydrocarbons of claim 1, wherein the overhead stream of the C8 separation column is condensed by heat exchange in one or more heat exchangers, and then a part of a condensed upper discharge stream from the C8 separation column is refluxed to the C8 separation column and a remaining part of the condensed upper discharge stream is supplied to the second extractive distillation column.

7. The method of producing aromatic hydrocarbons of claim 1, wherein an operation pressure of the C8 separation column is 100 mmHg to 350 mmHg.

8. The method of producing aromatic hydrocarbons of claim 1, wherein the raw material stream includes a C5 hydrocarbon to a C10 hydrocarbon.

9. The method of producing aromatic hydrocarbons of claim 1, wherein the discharge stream from the first gasoline hydrogenation unit is supplied to the first extractive distillation column, and benzene and toluene are separated as a lower discharge stream from the first extractive distillation column.

10. The method of producing aromatic hydrocarbons of claim 1, wherein the upper discharge stream from the second extractive distillation column is supplied to a second gasoline hydrogenation unit, and xylene is separated from a discharge stream from the second gasoline hydrogenation unit.

11. The method of producing aromatic hydrocarbons of claim 1, wherein the upper discharge stream from the second extractive distillation column includes a C8 aromatic hydrocarbon and the lower discharge stream from the second extractive distillation column includes a C8 vinyl aromatic hydrocarbon.

12. The method of producing aromatic hydrocarbons of claim 1, wherein the lower discharge stream from the C8 separation column includes C9+ hydrocarbons.

13. The method of producing aromatic hydrocarbons of claim 1, wherein the discharge stream from the first gasoline hydrogenation unit includes a C6 aromatic hydrocarbon and a C7 aromatic hydrocarbon.

14. The method of producing aromatic hydrocarbons of claim 1, wherein:
    the first gasoline hydrogenation unit is separately supplied with a raw material stream including a C5 hydrocarbon and a C6 hydrocarbon, and
    the raw material stream supplied to the first gasoline hydrogenation unit does not include styrene.

* * * * *